United States Patent [19]

Levitt et al.

[11] Patent Number: 4,831,054
[45] Date of Patent: May 16, 1989

[54] 2-ALKYL-3-BENZOYLBENZOFURANS USEFUL FOR TREATING CARDIAC ARRHYTHMIA

[75] Inventors: Barrie Levitt, Mamaroneck, N.Y.; Morris Stolar; Ron Breiman, both of Tel Aviv, Israel

[73] Assignee: Taro Pharmaceuticals, Ltd., Haifa Bay, Israel

[21] Appl. No.: 182,402

[22] Filed: Apr. 18, 1988

[51] Int. Cl.$^4$ .................... A61K 31/34; C07D 307/80
[52] U.S. Cl. ...................................... 514/469; 549/468
[58] Field of Search ..................... 549/468; 514/469

[56] References Cited

U.S. PATENT DOCUMENTS 3,012,042 12/1961 Hoi et al. ..................... 549/468
4,565,828 1/1986 Descamps et al. ............ 549/468

Primary Examiner—John M. Ford
Assistant Examiner—Bernard L. Dentz
Attorney, Agent, or Firm—Levonna Herzog

[57] ABSTRACT

New 2-alkyl-3-[4-(omega-N,N-dialkylaminoacylamino)-3,5-dialkylbenzoyl]benzofurans useful for treating cardiac arrhythmia, as well as pharmaceutical compositions containing these benzofurans and the method of treating cardiac arrhythmia therewith are disclosed.

19 Claims, No Drawings

2-ALKYL-3-BENZOYLBENZOFURANS USEFUL FOR TREATING CARDIAC ARRHYTHMIA

BACKGROUND OF INVENTION

This invention pertains to new alkylbenzoylbenzofurans and more particularly to new 2-alkyl-3-[4-(omega-N,N-dialkylaminoacylamino)-3,5-dialkylbenzoyl]benzofurans useful for treating cardiac arrhythmia, as well as pharmaceutical compositions containing these benzofurans and the method of treating cardiac arrhythmia therewith.

Cardiac arrhythmia is an important cause of death following myocardial infarction or from other cardiac pathology. Heretofore, drugs used to control this disorder such as quinidine, lidocaine and procainamide have manifested significant drawbacks. According to Goodman and Gilman, *The Pharmacologic Basis of Therapeutics*, 7th edition, pp.761–770, "About one third of the patients who receive quinidine will have immediate adverse effects that necessitate discontinuation of therapy . . . Procainamide is useful for the treatment of a variety of arrhythmias, and it can be administered by several routes. Unfortunately its potency and versatility are marred by its short duration of action and high incidence of adverse reactions when it is used chronically . . . Lidocaine has a narrow antiarrhythmic spectrum . . . The main adverse effects are on the central nervous system . . . Higher concentrations may cause decreased hearing, disorientation, muscle twitching, convulsions or respiratory arrest."

The great need for improved antiarrhythmics is evident.

SUMMARY OF THE INVENTION

An object of this invention is the provision of new compounds which have improved antiarrhythmic activity.

A particular object of this invention is the provision of new 2-alkyl-3-benzoylbenzofurans which have improved antiarrhythmic activity.

A further object of this invention is the provision of new pharmaceutical compositions useful for treating arrhythmia.

Another object of this invention is the provision of a new and improved method for treating arrhythmia.

These objects and others which will become evident from the description below are accomplished by our discovery of new 2-alkyl3-benzoylbenzofurans of the following formula (I)

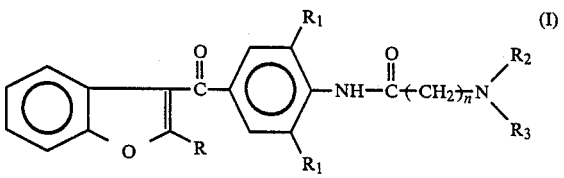

wherein
R is an alkyl group containing 2 to 4 carbon atoms,
$R_1$ is an alkyl group containing 1 to 4 carbon atom,
$R_2$ and $R_3$ are each an alkyl group containing 1 to 3 carbon atoms and
n is an integer of 1 or 2 and
pharmaceutically acceptable salts thereof.

We have found that compounds of formula (I) display highly significant antiarrhythmic activity and thus provide an improved method for the treatment of arrhythmia.

DESCRIPTION OF THE INVENTION

Compounds of formula (I) wherein R is $C_2H_5$, n-$C_3H_7$, and n-$C_4H_9$ are preferred, as are compounds of formula (I) wherein $R_1$ is $CH_3$, $C_2H_5$, i-$C_3H_7$ and t-$C_4H_9$. Another group of preferred compounds are those wherein $R_2$ and $R_3$ are both $C_2H_5$.

The preparation of compounds of formula (I) of the invention can be accomplished according to the following series of reactions.

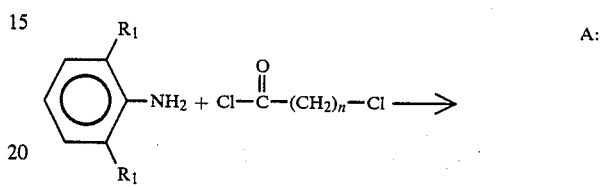

A:

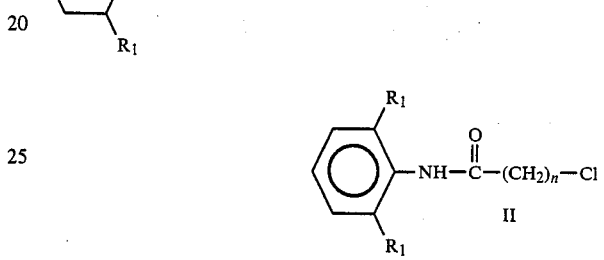

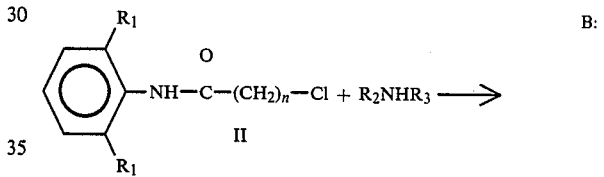

B:

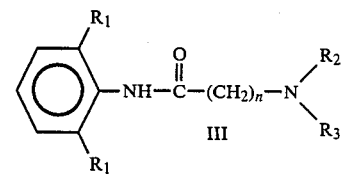

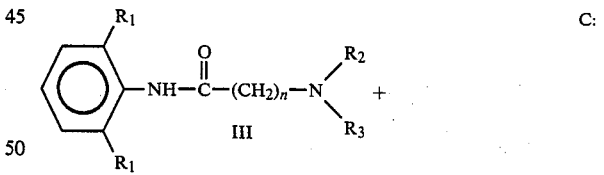

C:

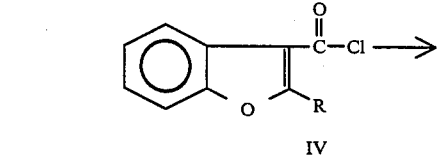

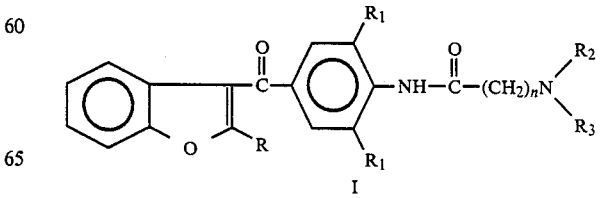

wherein R, $R_1$, $R_2$, $R_3$ and n are as defined above.

To prepare 2,6-dialkyl-alpha-chloroacetylanilide (II) where n=1 or 2,6-dialkyl-beta-chloropropionylanilide (II) where n=2 shown in step A, chloroacetyl chloride or beta-chloropropionyl chloride is reacted with a 2,6-dialkylaniline in an inert solvent such as a lower fatty acid or lower fatty acid ester, as described for example in U.S. Pat. No. 2,441,498.

The dialkyl-chloroacylanilide (II) is then reacted with a secamine in a refluxing hydrocarbon solvent as shown is step B. This reaction has also been described in the above-noted U.S. Patent. After separation and purification, the 2,6-dialkyl-omega-N,N-dialkylaminoacylanilide product (III) is obtained.

As shown in step C, compound (I) of the invention is obtained by reacting 2-alkylbenzofuran-3-carboxylic acid chloride (IV) with 2,6-dialkyl-omega-N,N-dialkylaminoacylanilide (III). This reaction is carried out in an inert solvent by means of a Friedel-Crafts system with a Lewis acid catalyst.

Compounds of the invention have improved antiarrhythmic activity. For example, 2-ethyl-3-[4-(N,N-diethylaminoacetylamino)-3,5-dimethylbenzoyl]benzofuran, (the compound of formula (I) wherein R=$C_2H_5$, $R_1$=$CH_3$, $R_2$ and $R_3$=$C_2H_5$ and n=1), when compared with lidocaine in a rat coronary ligation model, displayed superior activity in suppressing both ventricular fibrillation and ventricular tachycardia, and was comparable in promoting survival of challenged animals. Thus, compounds of formula (I) can provide an improved level of antiarrhythmic activity together with diminished side effects.

The antiarrhythmic compounds of formula (I) can be formulated for use by the oral or parenteral routes. Acute emergency treatment would normally employ an intravenous form containing as an active agent, a pharmaceutically acceptable salt such as the hydrochloride, sulfate, phosphate, etc. in an aqueous vehicle compatible with body fluids. The sterile, isotonic solution for such use is comprised of the soluble salt of the active drug in citrate, phosphate or other physiological acceptable buffer in the pH range of 4.0–7.0. Preservatives such as benzyl alcohol, methyl "Parabens" or propyl "Parabens", esters of p-hydroxybenzoic acid sold by Napp Chemicals, may be used, particularly in multiple dose formulations, to maintain sterility. Typical intravenous or intramuscular preparations may contain from 10–100 mg. of active compound, calculated as base, per ml. of solution. Administration of 0.5–10 mg. of active compound per kg. of patient body weight by the I.V. or I.M. route every 6–8 hours is continued until a satisfactory cardiac rhythm is established.

Chronic therapy is customarily maintained by means of oral tablets or capsules containing 10–200 mg. of a compound of formula (I) per dose. As is usual in this art, the active compound is admixed with excipients such as lactose, starch, "Avicel" or the like, together with lubricants and dispersants such as stearic acid, magnesium stearate, silica, etc. in amounts necessary to confer appropriate disintegration and dissolution properties to the dosage form.

The usual antiarrhythmic maintenance dose will be in the range of 1–100 mg. of active compound per kg. of patient body weight daily, delivered in 3 to 4 divided doses or in a single sustainedrelease dose.

The following examples further illustrate the invention but must not be construed to limit the invention in any manner.

EXAMPLE 1

Step A. Preparation of N-Acylaminoanilide (II) by Reaction of 2.6-Dialkylaniline with omega-Chloroacyl Chloride One mole of 2,6-dimethylaniline is dissolved in 800 ml. of glacial acetic acid. The mixture is cooled to 10° C., after which 1.1 mole of alpha-chloroacetyl chloride is added rapidly. The mixture is agitated vigorously for two minutes, whereupon 1000 ml. of aqueous sodium acetate (250 g. of sodium acetate per liter of water) is added rapidly with continuous agitation. Agitation is continued for one-half hour; the precipitate which has formed is separated by filtration, washed with water and dried carefully in vacuo at 50° C. The yield of 2,6-dimethyl-alpha-chloroacetanilide is 70–80% of the theoretical.

Following the same procedure, 2,6-diethylaniline, 2,6-diisopropylaniline or 2,6-di-tert-butylaniline is caused to react with alpha-chloroacetyl chloride to yield the corresponding alphachloro-2,6-dialkylacetanilide of formula (II).

Likewise any aniline identified above is caused to react with beta-chloropropionyl chloride to provide the corresponding betachloro-2,6-dialkyl-propionanilide of formula (II).

EXAMPLE 2

Step B. Preparation of N,N-Dialkylaminoacyl-2,6-dialkylanilide (III) by Reaction of omega-Chloroacyl-2,6-dialkylanilide (II) with a sec-Amine.

One mole of alpha-chloroacetyl-2,6-dimethylanilide and 3 moles of diethylamine are dissolved in 1000 ml. of dry benzene. The mixture is heated at reflux for 4 hours. The precipitated diethylamine hydrochloride is separated by filtration and the benzene solution is washed with 3 N hydrochloric acid twice (600 ml. each time). The aqueous acid extracts are made strongly basic by the addition of 30% aqueous sodium hydroxide. The resulting oily precipitate which separates is taken up in diethyl ether (1 liter), the ether phase is dried over anhydrous potassium carbonate, and the resulting dry, filtered ether solution is distilled. Following distillation of the ether at atmospheric pressure, the remainder of the fractionation is carried out in vacuo at about 2 mm. Hg. pressure. The product, alpha-diethylamino-2,6-dimethyl-acetanilide boils at about 159°–160° C. at 2 mm. Hg. It crystallizes in the receiver and the crystalline product melts at 68°–69° C. The yield is 95% of theoretical.

Using the same procedure, each of the three other alpha-chloro-2,6-dialkylacetanilides prepared as in Example 1 is caused to react with diethylamine to yield the corresponding alpha-diethyl-amino-2,6-dialkylacetanilide of formula (III).

Using the the same procedure, each of the four beta-chloropropionyl-2,6-dialkylanilides prepared according to Example 1 is caused to react with diethylamine to provide the corresponding beta-diethylaminopropionyl-2,6-dialkylanilide of formula (III).

When dimethylamine or dipropylamine is employed in this example, in place of diethylamine, the corresponding dimethylamino or dipropylamino product of formula (III), wherein both $R_2$ and $R_3$ are either $CH_3$ or $C_3H_7$, respectively, results.

EXAMPLE 3

Step C. Preparation of 2-Alkyl-3-[4-(omega-N,N-dialkylaminoacylamino)-3,5-dialkylbenzoyl]benzofuran (I) by Friedel-Crafts Acylation of the Anilide (III) with 2-Alkyl-3-benzofuroyl Chloride (IV)

2-Ethylbenzofuran-3-carboxylic acid chloride (0.45 g.;2.1 m.moles) and alpha-diethylamino-2,6-dimethyl-acetanilide (0.5 g.;2.1 m.moles)are dissolved in 1,2-dichloroethane (10 ml.) and cooled to 0° C. Anhydrous aluminum chloride (0.43 g.;3.2 m.moles) is added all at once and the reaction mixture is agitated for 16 hours at room temperature. The 1,2-dichloroethane solvent is then distilled off in vacuo and 10 ml. of 5 N aqueous hydrochloric acid is added to the residue. The resulting mixture is agitated for 30 minutes, made basic with aqueous sodium hydroxide and then extracted three times with 20 ml. portions of ethyl acetate. The ethyl acetate extracts are dried over anhydrous potassium carbonate and concentrated to a residue. The residue is taken up in a small volume of ethyl acetate and column chromatographed over 100 g. of anhydrous magnesium silicate. The column is eluted with hexane and mixtures of hexane and ethyl acetate, progressively enriched with ethyl acetate in the manner of gradient elution. Homogeneous product fractions, determined by TLC, are combined and crystallized from acetonehexane, affording 53 mg. of 2-ethyl-3-[4-(N,N-diethylaminoacetylamino)-3,5-dimethylbenzoyl]benzofuran (I), wherein $R=C_2H_5$, $R_1=CH_3$, $R_2$ and $R_3=C_2H_5$ and $n=1$, which has a melting point of 82°-85° C.

Reacting 2-n-propylbenzofuran-3-carboxylic acid chloride or 2-n-butylbenzofuran-3-carboxylic acid chloride with alpha-diethylamino-2,6-dimethyl-acetanilide (IV) in the same Friedel-Crafts procedure provides the corresponding 2-n-propyl- and 2-n-butylbenzofurans (I).

By reacting 2-ethylbenzofuran-3-carboxylic acid chloride with the dialkylanilide (III), wherein: $R_1=C_2H_5$, i-$C_3H_7$ or t-$C_4H_9$; $R_2=CH_3$ or n-$C_3H_7$ and $n=1$, the corresponding compounds of formula (I) are obtained wherein $R_1$ and $R_2$ are as follows:

| $R_1$ | $R_2$ and $R_3$ |
|---|---|
| $C_2H_5$ | $CH_3$ |
| $C_2H_5$ | n-$C_3H_7$ |
| i-$C_3H_7$ | $CH_3$ |
| i-$C_3H_7$ | n-$C_3H_7$ |
| t-$C_4H_9$ | $CH_3$ |
| t-$C_4H_9$ | n-$C_3H_7$ |

Reaction of the corresponding 2-n-propylbenzofuran-3-carboxylic acid chloride or 2-n-butylbenzofuran-3-carboxylic acid chloride (IV) affords corresponding compounds of formula (I) according to the choice of $R_1$ $R_2$ and $R_3$. Likewise compounds of formula (I) are provided wherein $n=2$, by reacting in the same manner a 2-alkylbenzofuran-3-carboxylic acid chloride (IV) with a beta-diethylaminopropionyl-2,6-dialkylanilide of formula (III).

EXAMPLE 4

Pharmaceutical Compositions

Injectable Composition for I.V. or I.M. Use

Compound (I)*: 50 mg.
Sodium citrate: 2 mg.
Sodium chloride: 14 mg.
Sterile water: 1 ml.

Tablets, 100 mg.

Compound (I)*: 100.0 mg.
"Avicel" ph 102: 83.35 mg.
Lactose, spray dried: 141.65 mg.
Magnesium stearate: 6.65 mg.
"Cab-O-Sil": 0.50 mg.

Tablets of the above formulation are prepared by blending all ingredients, except magnesium stearate, for 25 minutes, then adding the magnesium stearate and blending until homogeneous. The mixture is compressed into tablets using B/32 in standard concave molding. "Avicel" is a microcrystalline cellulose sold by FMC Corporation, Food & Pharmaceutical Products Division, while "Cab-O-Sil" is colloidal silica produced by the Cabot Corporation.

Tablets, 200 mg.

Compound (I)*: 200.0 mg.
"Avicel" ph 102: 144.0 mg.
Stearic acid powder: 9.0 mg.
Magnesium stearate: 3.2 mg.

Tablets are prepared from the above formulation by blending compound (I) with "Avicel" for 25 minutes, screening in the stearic acid and magnesium stearate and blending for 5 minutes more. The resultant mixture is compressed into tablets using ⅜ inch standard concave tooling.

Compound (I)* in each of the above formulations refers to the HCl form; however, the weight is the weight of the free base.

What we desire to claim and protect by Letters Patent is:

1. A 2-alkyl-3-benzoylbenzofuran of the formula

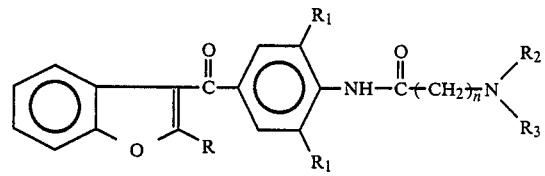

wherein
R is an alkyl group containing 2 to 4 carbon atoms,
$R_1$ is an alkyl group containing 1 to 4 carbon atom,
$R_2$ and $R_3$ are each an alkyl group containing 1 to 3 carbon atoms and
n is an integer of 1 or 2 and
pharmaceutically acceptable salts thereof.

2. The 2-alkyl-3-benzoylbenzofuran according to claim 1, in which R is an ethyl, n-propyl or n-butyl group.

3. The 2-alkyl-3-benzoylbenzofuran according to claim 1, in which R is an ethyl group.

4. The 2-alkyl-3-benzoylbenzofuran according to claim 1, in which $R_1$ is a methyl, ethyl, isopropyl or t-butyl group.

5. The 2-alkyl-3-benzoylbenzofuran according to claim 1, in which $R_1$ is a methyl group.

6. The 2-alkyl-3-benzoylbenzofuran according to claim 1, in which $R_2$ and $R_3$ are each a methyl, ethyl or propyl group.

7. The 2-alkyl-3-benzoylbenzofuran according to claim 1, in which $R_2$ and $R_3$ are each an ethyl group.

8. The 2-alkyl-3-benzoylbenzofuran according to claim 1, in which n is 1.

9. The 2-alkyl-3-benzoylbenzofuran according to claim 1, in which n is 2.

10. The 2-alkyl-3-benzoylbenzofuran according to claim 1, in which R is an ethyl, n-propyl, or n-butyl group, $R_1$ is a methyl group, $R_2$ and $R_3$ are each a methyl, ethyl or propyl group and n is 1.

11. The 2-alkyl-3-benzoylbenzofuran according to claim 1, in which R is an ethyl, n-propyl, or n-butyl group, $R_1$ is a methyl group, $R_2$ and $R_3$ are each a methyl, ethyl or propyl group and n is 2.

12. The 2-alkyl-3-benzoylbenzofuran according to claim 1, in which R is an ethyl group, $R_1$ is a methyl group and $R_2$ and $R_3$ are each a methyl, ethyl or propyl group.

13. The 2-alkyl-3-benzoylbenzofuran according to claim 1, which is 2-ethyl-3-[4-(N,N-diethylaminoacetylamino)-3,5-dimethylbenzoyl]benzofuran or a pharmaceutically acceptable salt thereof.

14. The 2-alkyl-3-benzoylbenzofuran according to claim 1, which is 2-ethyl-3-[4-(N,N-diethylamino-beta-propionylamino)-3,5-dimethylbenzoyl]benzofuran or a pharmaceutically acceptable salt thereof.

15. A pharmaceutical composition useful for treating cardiac arrhythmia comprising a compound according to claim 1 in a therapeutically effective amount in combination with a pharmaceutically acceptable carrier.

16. A pharmaceutical composition useful for treating cardiac arrhythmia comprising a compound according to claim 13 in a therapeutically effective amount in combination with a pharmaceutically acceptable carrier.

17. A pharmaceutical composition useful for treating cardiac arrhythmia comprising a compound according to claim 10 in a therapeutically effective amount in combination with a pharmaceutically acceptable carrier.

18. A pharmaceutical composition useful for treating cardiac arrhythmia in the form of an oral tablet comprising a compound according to claim 1 in a therapeutically effective amount in combination with a pharmaceutically acceptable carrier.

19. A method of treating a patient suffering from cardiac arrhythmia which comprises administering to said patient a therapeutically effective amount of a compound according to claim 1.

* * * * *